United States Patent
Gante et al.

[11] 3,980,795
[45] Sept. 14, 1976

[54] PYRAZOLIDINONES AND A PROCESS FOR THEIR PREPARATION

[75] Inventors: Joachim Gante; Hans-Adolf Kurmeier; Erich Schacht; Werner Mehrhof; Albrecht Wild, all of Darmstadt, Germany

[73] Assignee: Merck Patent Gesellschaft mit beschrankter Haftung, Darmstadt, Germany

[22] Filed: Nov. 5, 1975

[21] Appl. No.: 628,933

[30] Foreign Application Priority Data
Nov. 8, 1974 Germany............................ 2452946

[52] U.S. Cl.............................. 424/273; 260/310 A
[51] Int. Cl.².............. C07D 231/08; A61K 31/415
[58] Field of Search.................. 260/310 A; 424/273

[56] References Cited
UNITED STATES PATENTS
2,878,263  3/1959  Oroshnik ........................ 424/273
3,166,475  1/1965  Fiordalisi ........................ 424/273

FOREIGN PATENTS OR APPLICATIONS
1,200,548  7/1970  United Kingdom

OTHER PUBLICATIONS
Chemical Abstracts vol. 44;1491; vol. 58:14590h; vol. 72:6696g; vol. 73 p. 123506j; vol. 74:13401j.

Primary Examiner—Donald B. Moyer
Attorney, Agent, or Firm—Millen, Raptes & White

[57]  ABSTRACT

Pyrazolidinones of the formula

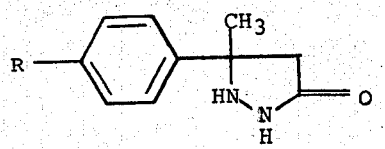

wherein R is a phenyl, phenoxy or a corresponding group monosubstituted or polysubstituted by one or more of F, Cl and Br possess anti-inflammatory activity.

14 Claims, No Drawings

PYRAZOLIDINONES AND A PROCESS FOR THEIR PREPARATION

BACKGROUND OF THE INVENTION

This invention relates to novel pyrazolidinones and to processes for their production and use.

SUMMARY OF THE INVENTION

In a composition aspect, this invention relates to novel pyrazolidinones of the general Formula I

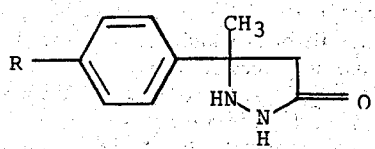

wherein R is a phenyl, phenoxy or a corresponding group monosubstituted or polysubstituted by one or more of F, Cl and Br.

In another composition aspect, this invention relates to pharmaceutical compositions comprising, in unit dosage form, an anti-inflammatorily effective amount of a compound of Formula I in admixture with a pharmaceutically acceptable carrier.

In process aspects, this invention relates to processes for the production and use of the compositions of this invention.

DETAILED DISCUSSION

The compounds of Formula I include 3-methyl-3-(4-biphenylyl)-pyrazolidin-5-ones, i.e., those wherein R is unsubstituted phenyl or phenyl monosubstituted or polysubstituted by F, Cl or Br and 3-methyl-3-(4-phenoxy-phenyl)-pyrazolidin-5-ones, i.e., wherein R is unsubstituted phenoxy or phenoxy monosubstituted or polysubstituted by F, Cl or Br). Of these, the biphenylyl compounds are preferred. Of the compounds of Formula I, those wherein R is an unsubstituted phenyl or phenoxy and, in particular, monosubstituted phenyl or phenoxy are preferred. Of the substituents, F is preferred followed by Cl. The substituents are preferably at the 4-position of the phenyl or phenoxy group, i.e., at the 4'-position of the biphenylyl radical when R is phenyl, with the 2'-position being the second preference. The phenyl or phenoxy group can, however, also be substituted in the 3-position. Of the polysubstituted phenyl or phenoxy groups, those which are disubstituted, particularly those which are disubstituted in the 2,4-position, are preferred. However, substitution in the 2,3-, 2,6-, 3,4- or 3,5-position is also possible, as well as trisubstitution in the 2,3,4-, 2,3,5-, 2,3,6-, 2,4,5-, 2,4,6-, or 3,4,5-position, tetra-substitution in the 2,3,4,5-, 2,3,4,6-or 2,3,5,6-position and penta-substitution in the 2,3,4,5,6-position. Of the polysubstituted phenyl or phenoxy radicals, those whose substituents are identical, for example, difluorophenyl, such as 2,4-difluorophenyl, difluorophenoxy, such as 2,4-difluorophenoxy, dichlorophenyl, such as 2,4-dichlorophenyl and dichlorophenoxy, such as 2,4-dichlorophenoxy, are preferred. Of the polysubstituted phenyl or phenoxy groups, those which are fluorosubstituted are preferred. Of those substituents which are different, those having at least one fluorine atom, for example, 2-fluoro-4-chlorophenyl, 2-chloro-4-fluorophenoxy, are preferred.

In preferred aspects, this invention relates to compounds of Formula I wherein R has one of the values indicated above.

In a process aspect, this invention relates to a process for the production of pyrazolidinones of Formula I wherein:

a. a hydrazine derivative of the general Formula II

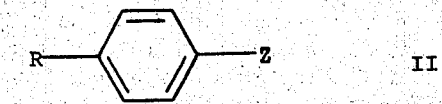

wherein Z is

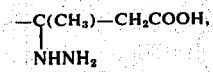

$-C(OH)(CH_3)-CH_2-CONHNH_2$, $-C(CH_3)=\lambda$ $CH-CONHNH_2$ or $-C(CH_3)=N-NH-CO-CH_2X$ and X is Cl, Br or I, and R has the values given above, or a functional derivative thereof, cyclized; or b. a compound of the general formula III

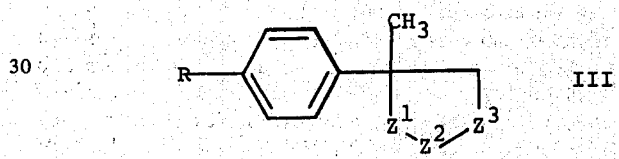

wherein $Z_1{}^1$ and $Z^2$ each are a free or functionally modified NH group; $Z^3$ is a free or functionally modified CO group; at least one of $Z^1$, $Z^2$ and $Z^3$ being functionally modified; and R has the values given above, is treated with a solvolyzing or hydrogenolyzing agent; or c. a compound of general Formula IV

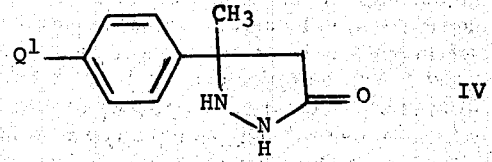

or a salt thereof, is reacted with a compound of the general Formula V

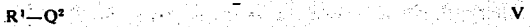

or with a salt thereof, wherein one of $Q^1$ and $Q^2$ is OH and the other is Y; $R^1$ is unsubstituted phenyl or phenyl monosubstituted or polysubstituted by F, Cl or Br; and Y is OH, Cl, Br, I or an OH group which is functionally modified in a reactive manner; or d. a compound of the general Formula VI

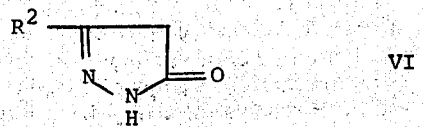

is reacted with a compound of the general Formula VII $R^3—M$            VII wherein one of $R^2$ and $R^3$ is

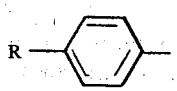 and the other is $CH_3$; M is one equivalent of a metal atom or of an organometallic radical, or is the MgX; and R and X have the values given above; and, if desired a thus-produced compound of Formula I wherein R is unsubstituted phenyl or phenoxy, is treated with a halogenating agent to produce a corresponding monosubstituted or polysubstituted phenyl or phenoxy group.

In all the general formulae hereinbefore or after, R has the values given for Formula I unless expressly indicated to the contrary.

In the compounds of Formula II, Z is preferably $—C(CH_3)(NHNH_2)—CH_2COOH$ or $—C(CH_3)=\lambda CH—CONHNH_2$ and X is preferably Br, and also Cl or I. Suitable functional derivatives of the compounds of Formula II are all those which can be cyclized to form pyrazolidinones of Formula I while simultaneously splitting off the functional group or groups, for example, the esters of the carboxylic acids indicated, particularly the alkyl esters wherein alkyl preferably is of 1–4 carbon atoms, and also, for example, thioesters and acid amides. Examples of other derivatives are those of the hydroxycarboxylic acid hydrazides (II, Z = $—C(OH)(CH_3)—CH_2—CONHNH_2$) in which the OH group is esterified, for example, in the form of a corresponding halogen derivative (Cl or Br instead of OH) or a lower acylate, preferably an alkanoate, wherein the acyl or alkanoyl radical preferably is up to 6 carbon atoms.

In the compounds of Formula III, preferably only one of $Z^1$, $Z^2$ and $Z^3$ is functionally modified. If $Z^1$ or $Z^2$ is functionally modified, they can be present, in particular, in the form of substituted NH groups wherein the substituent can be split off easily, e.g., can be solvolyzed or can be hydrogenolyzed, for example, in the form of an N-benzyl or N-carbobenzoxy group or another "protected" NH group known from peptide chemistry. If $Z^3$ is functionally modified, it preferably is $—C(=NH—$ or $—CS—$.

Suitable salts (phenolates) of the compounds of Formula IV and V are, preferably, the alkali metal salts, particularly the sodium salts. Y is preferably Br or Cl. When Y is an OH group which is functionally modified in a reactive manner, it preferably is alkylsulfonyloxy, in particular, those of 1–6 carbon atoms (for example, methylsulfonyloxy) or arylsulfonyloxy, in particular those of 6–10 carbon atoms (for example, benzenesulfonyloxy, p-toluenesulfonyloxy or naphthalenesulfonyloxy). In compounds of Formula VII, M is preferably Li or MgX and also Na, K, $ZnR^3$ and $CdR^3$.

In other respects, the preparation of the compounds of Formula I is carried out in accordance with methods which are in themselves known, such as are described in the literature (for example, in the standard works such as Houben-Weyl, Methoden der organischen Chemie (Methods of Organic Chemistry), Georg-Thieme-Verlag, Stuttgart), and under the reaction conditions which are known and suitable for the reactions mentioned.

If desired, the starting compounds for the preparation of the compounds of Formula I can also be formed in situ, i.e., they are not isolated from the reaction mixture but instead are immediately further reacted to form the compounds of Formula I.

The pyrazolidinones of Formula I preferably are obtained by cyclizing the hydrazine derivatives of Formula II.

The compounds of Formula II are new, but can be prepared by methods which are in themselves known. For example, it is possible to react ketones of the formula $p—R—C_6H_4—CO—CH_3$ with bromoacetic acid alkyl esters (preferably bromacetic acid ethyl ester) in the presence of zinc by the Reformatsky reaction to give hydroxy acid esters of the formula $p—R—C_6H_4—C(OH)(CH_3)—CH_2—COOalkyl$. If desired, these can be dehydrated to give the corresponding unsaturated esters of the formula $p—R—C_6H_4—C(CH_3)=\lambda CH—COOalkyl$. Reacting the hydroxy acid ester with $SOCl_2$ or $PBr_3$ gives the corresponding halogenated esters. The esters can be saponified to give the corresponding acids and these acids can be converted into the corresponding acid halides. Reacting the 3-chlorobutyric acids or 3-bromobutyric acids, which can be prepared in this way, of the formula $p—R—C_6H_4—C(CH_3)Cl—CH_2—COOH$ or $p—R—C_6H_4—C(CH_3)Br—CH_2—COOH$ with hydrazine gives the corresponding 3-hydrazino-carboxylic acids of Formula II [Z = $—C(NHNH_2)(CH_3)—CH_2COOH$]. Reacting the abovementioned hydroxy acid esters, or the abovementioned unsaturated esters, with hydrazine leads to the hydrazides of Formula II [Z = $—C(OH)(CH_3)—CH_2—CONHNH_2$ or $—C(CH_3)=\lambda CH—CONHNH_2$] or to the hydrazino-esters of the formula $p—R—C_6H_4—C(CH_3)(NHNH_2)—CH_2COOalkyl$.

The hydrazones of Formula II [Z = $—C(CH_3)=N—NH—CO—CH_2Y$] can be produced from the ketones mentioned above of the formula $p—R—C_6H_4—CO—CH_3$, employing hydrazides of the formula $H_2N—NH—CO—CH_2Y$ (for example, bromoacetic acid hydrazide).

In the abovementioned esters, alkyl preferably is of 1–4 carbon atoms.

It is particularly preferable not to isolate the compounds of Formula II, but to form them in situ, for example, from the carboxylic acids mentioned and reactive derivatives thereof, for example, the esters and halides mentioned or corresponding β-lactones, which are accessible from the ketones of the formula $p—R—C_6H_4—COCH_3$ and ketone. The hydrazones mentioned above of the Formula II are also accessible, for example, by reacting the ketones mentioned above with hydrazine to give the hydrazones of the formula $p—R—C_6H_4—C(CH_3)=N—NH_2$ and subsequently reacting, preferably in situ, the hydrazone with a derivative of a substituted acetic acid of the formula $CH_2Y—COOH$ (for example, bromoacetyl bromide).

The cyclization of the hydrazine derivatives of Formula II is generally carried merely by heating or by allowing a solution thereof in an inert solvent to stand or warming this solution. The reaction temperatures are preferably about 20 to about 150, particularly 60° to 110°. Examples of suitable solvents are alcohols, such as methanol, ethanol, propanol, isopropanol or n-butanol; ethers, such as diethyl ether, tetrahydrofuran (THF) or dioxane; hydrocarbons, such as benzene, toluene or xylene; nitriles, such as acetonitrile; amides, such as dimethylformamide (DMF); or sulfoxides, such as dimethylsulfoxide. The reaction times as a rule are about 0.5 to 24 hours. If the starting compound is produced in situ, the hydrazine used can be employed as such or in the form of hydrazine hydrate or it can also be liberated from one of its salts, for example, hydrazine sulfate or hydrazine hydrochloride, by the action of a base, such as sodium ethylate. Cyclization of the bromoacetic acid hydrazones of Formula II ($Z = -C(CH_3)=N-NH-CO-CH_2Br$) is preferably carried out by reduction under the conditions of the Reformatsky reaction in the presence of zinc, for example, zinc dust, preferably in a hydrocarbon, such as benzene or toluene, at the boiling point.

A particularly preferred method of preparing the pyrazolidinones of Formula I consists of boiling unsaturated esters of the formula $p-R-C_6H_4-C(CH_3)=CH-COOC_2H_5$ for several hours with hydrazine hydrate in an alcohol, such as ethanol.

A variant of the cyclization described above consists of employing starting compounds having a functional group modified in such a way that at least one of the NH groups and/or the CO group is still present in the reaction functionally modified form in the resulting cyclization product of Formula III. These functionally modified groups are then liberated by solvolysis, preferably hydrolysis, or hydrogenolysis, to obtain the pyrazolidinones of Formula I.

In the compounds of Formula III, $Z^1$ and/or $Z^2$ are, for example, NH groups which are substituted by a radical which can be split off by solvolysis, particularly an acyl radical of up to 7 carbon atoms, (for example, formyl, acetyl, propionyl, hexanoyl or benzoyl) or by a radical which can be split off by hydrogenolysis (for example, benzyl or carbobenzoxy). These compounds can be obtained, for example, by employing in the preparation of the starting materials described above one of the derivatives of hydrazine instead of hydrazine itself, for example, an acylhydrazine, such as acetylhydrazine, benzylhydrazine or carbobenzoxyhydrazine. The $Z^3$ radical in the compounds of Formula III can be, for example, $=NH$, $(O-alkyl)_2$ (wherein alkyl preferably is of up to 4 carbon atoms), or $=S$. These compounds can be obtained, for example, by employing the corresponding nitriles, ortho-esters or thio-esters instead of the abovementioned esters in the preparation of the starting compounds by reaction with hydrazine. Of the compounds of Formula III, preferred are those in which only one of $Z^1$, $Z^2$ and $Z^3$ is present in a functionally modified form.

Solvolysis, preferably hydrolysis, but also alcoholysis or ammonolysis, of the compounds of Formula III is carried out, for example, by treatment with an aqueous acid (for example, hydrochloric acid or sulfuric acid) or a base (for example, sodium hydroxide or potassium hydroxide). An inert organic solvent, such as methanol or ethanol, can be present as solubilizer. The temperatures in the solvolysis as a rule are from 20 to 100°. Care must be taken that the pyrazolidinone ring is not simultaneously opened in the solvolysis. Such opening of the ring can, however, be easily avoided by carrying out the reaction under relatively mild conditions (low temperatures and/or short reaction times).

A hydrogenolysis of the compounds of Formula III which contain groups which can be split by hydrogenolysis, is preferably carried out by the conventional methods of catalytic hydrogenation in the presence of a noble metal catalyst, such as platinum or palladium, and an inert organic solvent, for example, one of the above alcohols, at temperatures of about 0° to 100° and pressures of about 1 to 200 atmospheres, preferably at room temperature and ambient pressure.

The pyrazolidinones of Formula I can also be obtained by reacting a pyrazolidinone of Formula IV, or a salt thereof, with a compound of Formula V or a salt thereof.

The starting compounds of Formula IV can be obtained, for example, by reaction of $p-Q^1$-acetophenones with bromoacetic acid alkyl esters and zinc to give hydroxy esters of the formula $p-Q^1-C_6H_4-C(CH_3)(OH)-CH_2-COOalkyl$ and subsequent dehydration and reaction with hydrazine. The starting compounds of Formula V for the most part are known.

It is possible to react either a phenol of Formula IV ($Q^1=OH$) with a compound of Formula V ($Q^2=Y$) or a compound of Formula IV ($Q^1=Y$) with a phenol of Formula V ($Q^2=OH$). In this reaction, the phenols are preferably in the form of the corresponding phenolates, particularly the corresponding sodium phenolates or potassium phenolates. The reaction is preferably carried out in the presence of an inert solvent, such as DMF or phosphoric acid hexamethyltriamide, in the presence of a catalyst, such as copper powder, at temperatures of about 50 to about 200, preferably 80° to 130°.

The pyrazolidinones of Formula I can also be obtained by reacting the pyrazolinones of Formula VI with organometallic compounds of Formula VII.

The starting compounds of Formula VI can be prepared, for example, by reacting keto-esters of the formula $R^2-CO-CH_2-COOalkyl$, for example, 3-(4-biphenylyl)- or 3-(4-phenoxyphenyl)-3-oxo-propionic acid alkyl esters or acetoacetic acid alkyl esters, with hydrazine. The compounds of Formula VII (for example, 4-biphenylyl-lithium or 4-biphenylyl-magnesium bromide or iodide, 4-phenoxyphenyl-lithium or 4-phenoxyphenyl-magnesium bromide or iodide, or methyl-lithium or methyl-magnesium bromide or iodide) are for the most part known. The reaction of the compounds VI and VII is carried out under known conditions for a Grignard reaction, preferably in an inert solvent, for example, an ether, such diethyl ether, diisopropyl ether, THF or dioxane, at temperatures of about 0° to about 100°, preferably 10° to 40°. It is advantageous to add a solution of the compound VI dropwise, while stirring, to a solution of the compound VII. The reaction mixture is then hydrolyzed in the conventional manner, for example, using dilute mineral acids, such as hydrochloric acid, or using ammonium chloride solution.

In addition, in a resulting compound of Formula I wherein R is unsubstituted phenyl or phenoxy, a chlorine or bromine atom can be introduced by halogenation in accordance with methods described in the literature, so that a chlorine-substituted or bromine-substituted compound of Formula I is obtained. This is possible, for example, by direct reaction with chlorine or bromine in an inert solvent, such as ether, tetrachloromethane or acetic acid, preferably at temperatures of −30° to 100°. A catalyst, for example iron fillings, iodine or $AlCl_3$, can be present.

The compounds of Formula I contain a center of asymmetry and are usually present in the racemic form. These racemates can be resolved into their optical antipodes with the aid of known methods described in the literature. It is also possible to obtain optically active compounds of Formula I by using optically active starting materials in accordance with known methods.

The compounds of Formula I are well tolerated and possess valuable pharmacological properties, in particular, antiphlogistic activity which can be demonstrated in rats, for example, in the adjuvans-arthritis test by the method of Newbould (Brit. J. Pharmacol. 21. (1963) 127–136). They also possess serum cholesterol level-lowering and triglyceride level-lowering activity which can be demonstrated in the serum of rats by the method of Levine et al. (Automation in Analytical Chemistry, Technicon Symposium 1967, Mediad, New York, pages 25–28) or by the method of Noble and Campbell (Clin. Chem. 16 (1970), pages 166–170). In addition, analgesic, enzyme-inducing and fibrinolytic activity and activity which inhibits the aggregation of thrombocytes can be observed by methods which are currently employed for these purposes.

The compounds of Formula I can, therefore, be used as medicaments and are also useful as intermediate products for the preparation of other medicaments.

The compounds of Formula I can be used, mixed with solid, liquid and/or semi-liquid medicinal excipients, as medicaments in human and veterinary medicine. Excipients which can be used are organic or inorganic substances which are suitable for parenteral or enteral administration or topical application and which do not react with the new compounds, for example, water, vegetable oils, benzyl alcohols, poly-ethylene glycols, gelatine, lactose, starch, magnesium stearate, talc, petroleum jelly or cholesterol. Solutions, preferably oily or aqueous solutions, and supensions, emulsions, or implants, are particularly used for parenteral administration. Tablets, dragees, capsules, syrups, elixirs, drops or suppositories are suitable for enteral administration, and ointments, creams or powders are suitable for topical application. such preparations can be sterilized or can contain auxiliaries, such as lubricants, preservatives, stabilizers or wetting agents, emulsifiers, salts for controlling osmotic pressure, buffer substances, colorants, flavorings and/or aroma substances. If desired, they can also contain one or more other active substances, for example, one or more vitamins.

The novel compounds of Formula I are generally administered analogously to known, commercially available antiphlogistics, preferably in dosages from 10 to 1,000 mg, particularly 30 to 300 mg, per dosage unit. The daily dosage is preferably about 0.2 to 20 mg/kg of body weight. Oral administration is preferred.

The compounds of Formula I named in the examples which follow are particularly suitable for the production of pharmaceutical preparations.

Without further elaboration, it is believed that one skilled in the art can, using the preceding description utilized the present invention to its fullest extent. The following preferred specific embodiments are, therefore, to be construed as merely illustrative, and not limitative of the remainder of the disclosure in any way whatsoever.

In the preceding and following text, temperatures are in degrees Centigrade. "Usual work up" means as follows: if necessary, water and/or an organic solvent, such as benzene, chloroform or dichloromethane are added, the phases are separated, the organic phase is dried over sodium sulfate, filtered and evaporated and the product is purified by chromatography and/or crystallization.

Preparation a. A solution of 29.0 g 4-p-fluorophenylacetophenone in 340 ml of benzene is reacted for 2 hours at 80° with 22.6 g bromoacetic acid ethyl ester and 10.7 g zinc, cooled, mixed with 100 ml of 2n sulfuric acid and worked up in the usual manner to give 3-(4'-fluoro-4-biphenylyl)-3-hydroxybutyric acid, m.p. 81° – 82°.

b. A solution of 105.5 g 3-(4'-fluoro-4-biphenylyl)-3-hydroxybutyric acid and 5.3 g p-toluenesulfonic acid in 1500 ml of toluene is heated for 2,5 hours and worked up in the usual manner to give 3-(4'-fluoro-4-biphenylyl)-2-butenoic acid, m.p. 58° – 60°.

EXAMPLE 1

28.8 g of 3-(4'-fluoro-4-biphenylyl)-3-hydroxybutyric acid hydrazide [obtainable by Friedel-Crafts acetylation of 4-fluorobiphenyl to give 4-p-fluorophenylacetophenone, reaction with bromoacetic acid ethyl ester/zinc to give 3-(4'-fluoro-4-biphenylyl)-3-hydroxybutyric acid ethyl ester and reaction with hydrazine hydrate in ethanol] in 200 ml of DMF is heated and worked up in the customary manner to give 3-(4'-fluoro-4-biphenylyl)-3-methyl-pyrazolidin-5-one, m.p. 194°–196°.

EXAMPLE 2

A mixture of 30.2 g of 3-(4'-fluoro-4-biphenylyl)-3-hydroxybutyric acid ethyl ester and 25 g of 100% strength hydrazine hydrate is heated at 100° for 4 hours. The mixture is worked up in the usual manner to give 3-(4'-fluoro-4-biphenylyl)-3-methyl-pyrazolidin-5-one, m.p. 194°–196 °.

EXAMPLE 3

A solution of 36.5 g of 3-bromo-3-(4'-fluoro-4-biphenylyl)-butyric acid ethyl ester [obtainable from 3-(4'-fluoro-4-biphenylyl)-3-hydroxybutyric acid ethyl ester and $PBr_3$] and 7 g of hydrazine in 200 ml of dioxane is boiled for 2 hours and is evaporated. Working up gives 3-(4'-fluoro-4-biphenylyl)-3-methyl-pyrazolidin-5-one, m.p. 194°–196°.

Analogously, 3-chloro-3-(4-biphenylyl)-butyric acid methyl ester and hydrazine give 3-(4-biphenylyl)-3-methylpyrazolidin-5-one, m.p. 191°–192°.

EXAMPLE 4

A solution of 32.1 g of 3-chloro-3-(4'-fluoro-4-biphenylyl)-butyric acid ethyl ester (obtainable from the hydroxy ester and SOCl$_2$), 15 g of hydrazine sulfate and 20.5 g of sodium ethylate in 500 ml of absolute ethanol is boiled for 2 hours and the solvent is evaporated. Working up gives 3-(4'-fluoro-4-biphenylyl)-3-methyl-pyrazolidin-5-one, m.p. 194°–196°.

EXAMPLE 5

A solution of 28.4 g of 3-(4'-fluoro-4-biphenylyl)-2-butenoic acid ethyl ester [obtainable by dehydrating 3-(4'-fluoro-4-biphenylyl)-3-hydroxybutyric acid ethyl ester employing p-toluenesulfonic acid] and 25 g of hydrazine hydrate (100% strength) in 400 ml of ethanol is boiled for 18 hours. The mixture is cooled, poured onto ice water and worked up in the usual manner to give 3-(4'-fluoro-4-biphenylyl)-3-methyl-pyrazolidin-5-one, m.p. 194°–196°.

The following are obtained analogously from the corresponding 3-aryl-2-butenoic acid methyl or ethyl esters by reaction with hydrazine hydrate:

3-(4-biphenylyl)-3-methyl-pyrazolidin-5-one, m.p. 191°–192°,
3-(2'-fluoro-4-biphenylyl)-3-methyl-pyrazolidin-5-one, m.p. 167°–168°,
3-(3'-fluoro-4-biphenylyl)-3-methyl-pyrazolidin-5-one, m.p. 173°–175°,
3-(2',4'-difluoro-4-biphenylyl)-3-methyl-pyrazolidin-5-one,
3-(2',3',4',5',6'-pentafluoro-4-biphenylyl)-3-methyl-pyrazolidin-5-one,
3-(2'-chloro-4-biphenylyl)-3-methyl-pyrazolidin-5-one,
3-(3'-chloro-4-biphenylyl)-3-methyl-pyrazolidin-5-one, 3-(4'-chloro-4-biphenylyl)-3-methyl-pyrazolidin-5-one, m.p. 214°–215°,
3-(2',4'-dichloro-4-biphenylyl)-3-methyl-pyrazolidin-5-one,
3-(2'-fluoro-4'-chloro-4-biphenylyl)-3-methyl-pyrazolidin-5-one,
3-(2'-chloro-4'-fluoro-4-biphenyly)-3-methyl-pyrazolidin-5-one,
3-(2'-bromo-4-biphenylyl)-3-methyl-pyrazolidin-5-one,
3-(3'-bromo-4-biphenylyl)-3-methyl-pyrazolidin-5-one,
3-(4'-bromo-4-biphenylyl)-3-methyl-pyrazolidin-5-one,
3-(2',4'-dibromo-4-biphenylyl)-3-methyl-pyrazolidin-5-one,
3-(2'-fluoro-4'-bromo-4-biphenylyl)-3-methyl-pyrazolidin-5-one,
3-(2'-bromo-4'-fluoro-4-biphenylyl)-3-methyl-pyrazolidin-5-one,
3-(4-phenoxy-phenyl)-3-methyl-pyrazolidin-5-one,
3-(4-o-fluorophenoxy-phenyl)-3-methyl-pyrazolidin-5-one,
3-(4-m-fluorophenoxy-phenyl)-3-methyl-pyrazolidin-5-one,
3-(4-p-fluorophenoxy-phenyl)-3-methyl-pyrazolidin-5-one,
3-[4-(2,4-difluorophenoxy)-phenyl]-3-methyl-pyrazolidin-5-one,
3-[4-(2,3,4,5,6-pentafluorophenoxy)-phenyl]-3-methyl-pyrazolidin-5-one,
3-(4-o-chlorophenoxy-phenyl)-3-methyl-pyrazolidin-5-one,
3-(4-m-chlorophenoxy-phenyl)-3-methyl-pyrazolidin-5-one,
3-(4-p-chlorophenoxy-phenyl)-3-methyl-pyrazolidin-5-one,
3-[4-(2,4-dichlorophenoxy)-phenyl]-3-methyl-pyrazolidin-5-one,
3-[4-(2-fluoro-4-chlorophenoxy)-phenyl]-3-methyl-pyrazolidin-5-one,
3-[4-(2-chloro-4-fluorophenoxy)-phenyl]-3-methyl-pyrazolidin-5-one,
3-(4-o-bromophenoxy-phenyl)-3-methyl-pyrazolidin-5-one,
3-(4-m-bromophenoxy-phenyl)-3-methyl-pyrazolidin-5-one,
3-(4-p-bromophenoxy-phenyl)-3-methyl-pyrazolidin-5-one,
3-[4-(2,4-dibromophenoxy)-phenyl]-3-methyl-pyrazolidin-5-one,
3-[4-(2-fluoro-4-bromophenoxy)-phenyl]-3-methyl-pyrazolidin-5-one and
3-[4-(2-bromo-4-fluorophenoxy)-phenyl]-3-methyl-pyrazolidin-5-one.

EXAMPLE 6

25.6 g of 3-(4'-fluoro-4-biphenylyl)-3-hydroxybutanoic acid lactone (obtainable from 4-p-fluorophenyl-acetophenone and ketene) is boiled for 3 hours with 25 g of 100% strength hydrazine hydrate in 500 ml of methanol, and the mixture is cooled, poured onto ice and worked up in the usual manner to give 3-(4'-fluoro-4-biphenylyl)-3-methyl-pyrazolidin-5-one, m.p. 194°–196°.

EXAMPLE 7

A mixture of 34.9 g of 4-p-fluorophenyl-acetophenone-(bromoacetylhydrazone) (obtainable from 4-p-fluorophenylacetophenone and bromoacetic acid hydrazide), 150 ml of toluene and 7 g of zinc dust (previously washed successively with 1% strength hydrochloric acid, water and acetone and dried) is boiled for one hour, cooled and decomposed with half-concentrated hydrochloric acid. Separating the phases and washing and evaporating the toluene phase gives 3-(4'-fluoro-4-biphenylyl)-3-methyl-pyrazolidin-5-one, m.p. 194°–196°.

EXAMPLE 8

11.1 ml of bromoacetic acid ethyl ester are dissolved in a mixture of 75 ml of benzene and 75 ml of toluene. Part (40 ml) of the resulting solution is added to 7 g of zinc powder (previously washed successively with 1% strength hydrochloric acid, water and acetone and dried) and the mixture is warmed to 70° while stirring and passing in nitrogen. After the reaction has begun, the rest of the solution is added dropwise, followed by a solution of 22.8 g of 4-p-fluorophenyl-acetophenone hydrazone in 250 ml of benzene. The mixture is then boiled for one hour. 3-Hydrazino-3-(4'-fluoro-4-biphenylyl)-butyric acid ethyl ester is probably formed as an intermediate product. The mixture is cooled and 40 ml of 20% strength sulfuric acid are added dropwise. The organic phase is separated off, washed with water and evaporated. 3-(4'-fluoro-4-biphenylyl)-3-methyl-pyrazolidin-5-one, m.p. 194°–196°, is obtained.

EXAMPLE 9

26.9 g of 3-(4'-fluoro-4-biphenylyl)-3-methyl-5-imino-pyrazolidine [obtainable from 3-(4'-fluoro-4-biphenylyl)-2-butenoic acid nitrile and hydrazine] are boiled for 10 minutes with 150 ml of 20% strength aqueous hydrochloric acid and 150 ml of ethanol, and the solution is concentrated, neutralized and worked up in the usual manner to give 3-(4'-fluoro-4-biphenylyl)-3-methyl-pyrazolidin-5-one, m.p. 194°–196°.

EXAMPLE 10

26.9 g of 3-(4'-fluoro-4-biphenylyl)-3-methyl-5-imino-pyrazolidine are boiled for 10 minutes with 150 ml of 2 N aqueous potassium hydroxide solution and 150 ml of isopropanol and the mixture is worked up in the usual manner to give 3-(4'-fluoro-4-biphenylyl)-3-methyl-pyrazolidin-5-one, m.p. 194°–196°.

EXAMPLE 11

A solution of 1 g of a mixture of 1- and 2-benzyl-3-(4-biphenylyl)-3-methyl-pyrazolidin-5-one [obtainable from 3-(4-biphenylyl)-2-butenoic acid ethyl ester and benzylhydrazine] in 30 ml of methanol is hydrogenated over 300 mg of 5% strength Pd-on-charcoal at 20° and ambient pressure until absorption of hydrogen has ceased. The mixture is filtered and evaporated to give 3-(4-biphenylyl)-3-methyl-pyrazolidin-5-one, m.p. 191°–192°.

EXAMPLE 12

A mixture of 22.2 g of p-iodofluorobenzene and 21.4 g of the sodium salt of 3-p-hydroxyphenyl-3-methyl-pyrazolidin-5-one (obtainable by the reaction of p-hydroxyacetophenone with bromoacetic acid ethyl ester/zinc to give 3-hydroxy-3-p-hydroxyphenylbutyric acid ethyl ester, dehydration to give 3-p-hydroxyphenyl-2-butenoic acid ethyl ester and reaction with hydrazine hydrate) is warmed for 8 hours at 90° in the presence of 10 g of Cu powder in 100 ml of phosphoric acid hexamethyltriamide. The usual working up gives 3-(4'-fluoro-4-biphenylyl)-3-methyl-pyrazolidin-5-one, m.p. 194°–196°.

EXAMPLE 13

A solution of 30.2 g of 3-p-iodophenyl-3-methyl-pyrazolidin-5-one (obtainable from p-iodoacetophenone via 3-hydroxy-3-p-iodophenyl-butyric acid ethyl ester and 3-p-iodophenyl-2-butenoic acid ethyl ester) and 13.4 g of sodium p-fluorophenolate in 200 ml of DMF is warmed for 8 hours at 130°. Working up in the usual manner gives 3-(4'-fluoro-4-biphenylyl)-3-methyl-pyrazolidin-5-one, m.p. 194°–196°.

EXAMPLE 14 a. A solution of 23.6 g of 3-(4-biphenylyl)-pyrazolin-5-one [obtainable from 3-(4-biphenylyl)-3-oxopropionic acid ethyl ester and hydrazine] in 400 ml of THF is added dropwise, while stirring and cooling, to a Grignard solution prepared from 4.8 g of magnesium and 28.4 g of methyl iodide in 800 ml of absolute THF. After stirring for 2 hours at 10°–25°, the mixture is decomposed with ice and dilute hydrochloric acid and worked up in the usual manner to give 3-(4-biphenylyl)-3-methyl-pyrazolidin-5-one, m.p. 191°–192°.

b. 25.2 g of 3-(4-biphenylyl)-3-methyl-pyrazolidin-5-one are dissolved in 200 ml of acetic acid, a solution of 7.1 g of chlorine in 200 ml of acetic acid is added dropwise while stirring, and the mixture is stirred for a further hour and evaporated. Working up in the usual manner gives 3-(4'-chloro-4-biphenylyl)-3-methyl-pyrazolidin-5-one, m.p. 214°–215°.

c. Analogously to b), 3-(4-biphenylyl)-3-methyl-pyrazolidin-5-one and the calculated theoretically required quantity of bromine in acetic acid give 3-(4'-bromo-4-biphenylyl)-3-methyl-pyrazolidin-5-one.

EXAMPLE 15

A solution of 9.8 g of 3-methyl-pyrazolin-5-one in 100 ml of THF is added dropwise with stirring and cooling, to a Grignard solution prepared from 4.8 g of magnesium and 20.3 g of 4-bromo-4'-fluoro-biphenyl in 800 ml of absolute ether. After stirring for 2 hours at 10°–25°, the mixture is decomposed with ice and dilute hydrochloric acid and worked up in the usual manner to give 3-(4'-fluoro-4-biphenylyl)-3-methyl-pyrazolidin-5-one, m.p. 194°–196°.

The examples below relate to pharmaceutical preparations which contain an active compound of Formula I.

EXAMPLE A: Tablets

A mixture consisting of 1 kg of 3-(4'-fluoro-4-biphenylyl)-3-methyl-pyrazolidin-5-one, 4 kg of lactose, 1.2 kg of wheat starch, 0.2 kg of talc and 0.1 kg of magnesium stearate is pressed into tablets in the customary manner, in such a way that each tablet contains 100 mg of active compound.

EXAMPLE B: Dragees

Analogously to Example A, tablets are pressed which are then coated in the usual manner with a coating consisting of sugar, maize starch, talc and tragacanth.

EXAMPLE C: Capsules 5 kg of 3-(4'-fluoro-4-biphenylyl)-3-methyl-pyrazolidin-5-one are filled into hard gelatine capsules in the usual manner in such a way that each capsule contains 250 mg of the active compound.

Tablets, dragees and capsules which contain one or more of each of the other compounds of Formula I can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A pyrazolidinone of the formula

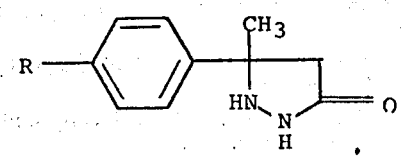

wherein R is phenyl, phenoxy or a corresponding group monosubstituted or polysubstituted by at least one of F, Cl and Br.

2. A compound of claim 1 wherein R is phenyl or phenyl monosubstituted or disubstituted by one or both of F and Cl.

3. A compound of claim 1 wherein R is phenyl monosubstituted or disubstituted by F.

4. A compound of claim 1 wherein R is phenoxy monosubstituted or disubstituted by one or both of F and Cl.

5. A compound of claim 1 wherein R is phenoxy monosubstituted by one of F and Cl.

6. A compound of claim 1, 3-(4-biphenylyl)-3-methyl-pyrazolidin-5-one.

7. A compound of claim 1, 3-(2'-fluoro-4-biphenylyl)-3-methyl-pyrazolidin-5-one.

8. A compound of claim 1, 3-(4'-fluoro-4-biphenylyl-3-methyl-pyrazolidin-5-one.

9. A compound of claim 1, 3-(2',4'-difluoro-4-biphenylyl)-3-methyl-pyrazolidin-5-one.

10. A compound of claim 1, 3-(4'-chloro-4-biphenylyl)-3-methyl-pyrazolidin-5-one.

11. A compound of claim 1, 3-[4-(4-fluorophenoxy)-phenyl]-3-methyl-pyrazolidin-5one.

12. A compound of claim 1, 3-[4-(4-chlorophenoxy)-phenyl]-3-methyl-pyrazolidin-5-one.

13. A pharmaceutical composition comprising, in unit dosage form, a compound of claim 1 in admixture with a pharmaceutically acceptable carrier.

14. A method treating inflammatory conditions which comprises administering systemically to the affected patient an anti-inflammatorily effective amount of a compound of claim 1.

* * * * *